Figure 1:
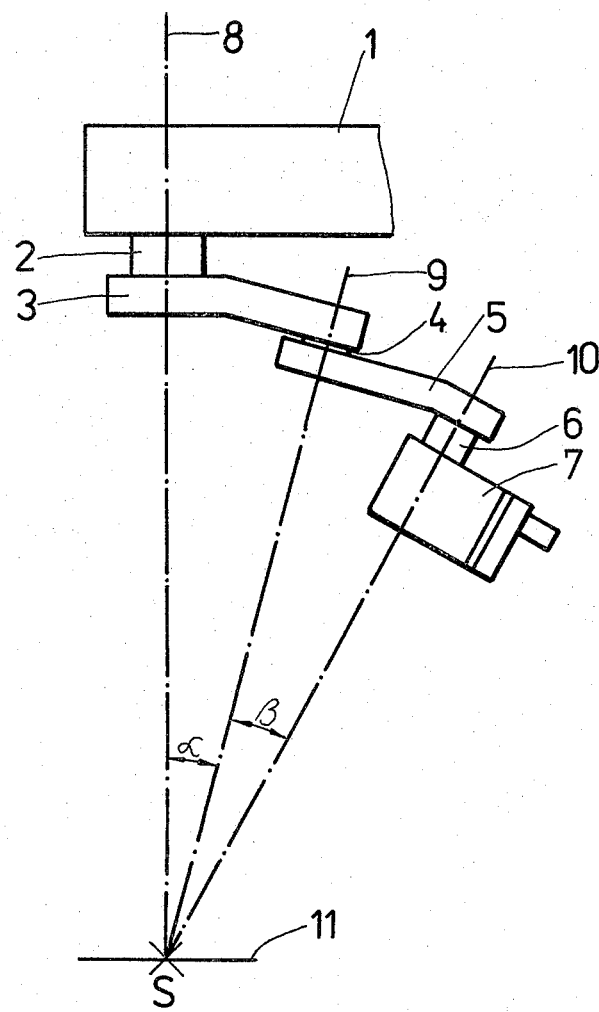

United States Patent [19]

Rüdel

[11] 4,290,666
[45] Sep. 22, 1981

[54] JOINT FOR AN OBSERVATION DEVICE

[76] Inventor: Reinhard Rüdel, 8, Hermann-Matern-Strasse, JENA-Lobeda, District of Gera, German Democratic Rep.

[21] Appl. No.: 96,303

[22] Filed: Dec. 11, 1979

[30] Foreign Application Priority Data

Nov. 24, 1928 [DD] German Democratic Rep. ... 209288

[51] Int. Cl.³ .......................... G02B 7/24; G02B 23/16
[52] U.S. Cl. .................................................... 350/85
[58] Field of Search ........................ 350/85, 82, 81, 33

[56] References Cited

U.S. PATENT DOCUMENTS

| 2,967,458 | 1/1961 | Stone | 350/85 |
| 3,762,796 | 10/1973 | Heller | 350/85 |
| 3,887,267 | 6/1975 | Heller | 350/85 |
| 3,891,301 | 6/1975 | Heller | 350/85 |

FOREIGN PATENT DOCUMENTS 2002214 1/1969 France ................................. 350/85

Primary Examiner—Jon W. Henry

[57] ABSTRACT

The invention concerns a joint for an observation device as an accessory to or a component of ophthalmological devices or surgical microscopes. The invention permits the folding of the object side optical axis of said device in such a manner that at any desired rotation about pivots respective inclinations of the observation beam relative to the object are obtained without the object migrating out of the field of view and without reversing the object image. Furthermore, the invention enables a continuous angular adjustment and a non-varying position of the entrance pupils of the device. This is achieved by directing a non-displaceable axis of rotation at right angles to the observation plane. The displaceable axis of rotation and the observation beam include angles relative to each other and have a common vertex in the observation plane.

3 Claims, 2 Drawing Figures

JOINT FOR AN OBSERVATION DEVICE

The invention concerns a joint for an observation device, particularly for use in ophthalmologic devices and in surgical microscopes.

When observing small three-dimensional objects from the medical field, it is necessary to tilt the observation device about different angles so to obtain diverse observation directions. This is achieved in the previous devices as follows: The axes of rotation and tilt, respectively, are arranged in the vicinity of the center of gravity of a device. This arrangement is disadvantageous since the axes of rotation are comparatively widely spaced apart to the object field of the device so that the latter is displaced by considerable amounts even at small tiltings of the device about one of these axes.

The displacements have to be compensated for through a comparatively expensive new adjustment of the device. In a further known arrangement the two axes of rotation intersect at right angles in one plane in the point S. The plane defined through the two axes of rotation contacts the pupil of an eye and the object, respectively.

The point of intersection S lies in the object axis. One of the two axes is obtained virtually through a slide guide bearing or through a double parallelogram. A displacement of the object field in the event of tilting of the device is eliminated in this arrangement.

However, the decisive drawback of the arrangement lies in the fact that the pupils of the device follow the tiltings of the device and migrate along an arc or a calotte, that is, the operator's attitude has to follow the tilting of the device.

In further known arrangements reflectors and prisms, respectively, are used to vary the observation angle, as disclosed in the West German Utility Models Nos. 7 006 558 and 7 305 091, respectively.

These arrangements are disadvantageous since, due to non-displaceable reflector positions, one observation angle can be set only.

It is an object of the present invention to obviate the above disadvantages.

It is a further object of the present invention to provide a joint for an observation device which folds the object side optical axis in such a manner that tiltings of the observation beam to the object are obtained at any desired rotation about the mechanical joint axles without the object migrating out of the field of view and without reversing the image of the object.

It is still a further object of the invention to maintain the position of the pupils of a device in spite of a tilting of the latter.

These and other objects of the invention are realised in a joint for an observation device which permits a continuous angular adjustment and a tilting of said device comprising at least two joint members, an end portion of the first of which is seated for rotation in a fixed part of said device, and a second joint member is seated for rotation in the other end portion of said first joint member.

The axis of rotation of the first joint member is non-displaceably arranged and substantially at right angles to the observation plane. The axes of rotation of the further joint members are displaceable and include an angle with the axial beam of the observation device.

The common vertex of the axes and of the axial beam lies in the observation plane.

The angle included between two axes of rotation associated to one and the same joint member is constant.

Advantageously, the axial beam emitting from out of the observation device coincides with the remote displaceable axis of rotation and partially coincides with the non-displaceable axis of rotation.

It is a further advantage when the axial beam is directed through the joint members by means of reflectors arranged in couples at each of the joint elements and when the axial beam between the reflectors of one joint member and the subsequent one coincides with the respective axis of rotation and when the observation beam emitting from out of the last joint member includes a constant angle with the axis of rotation of said last joint member.

Figure 2:
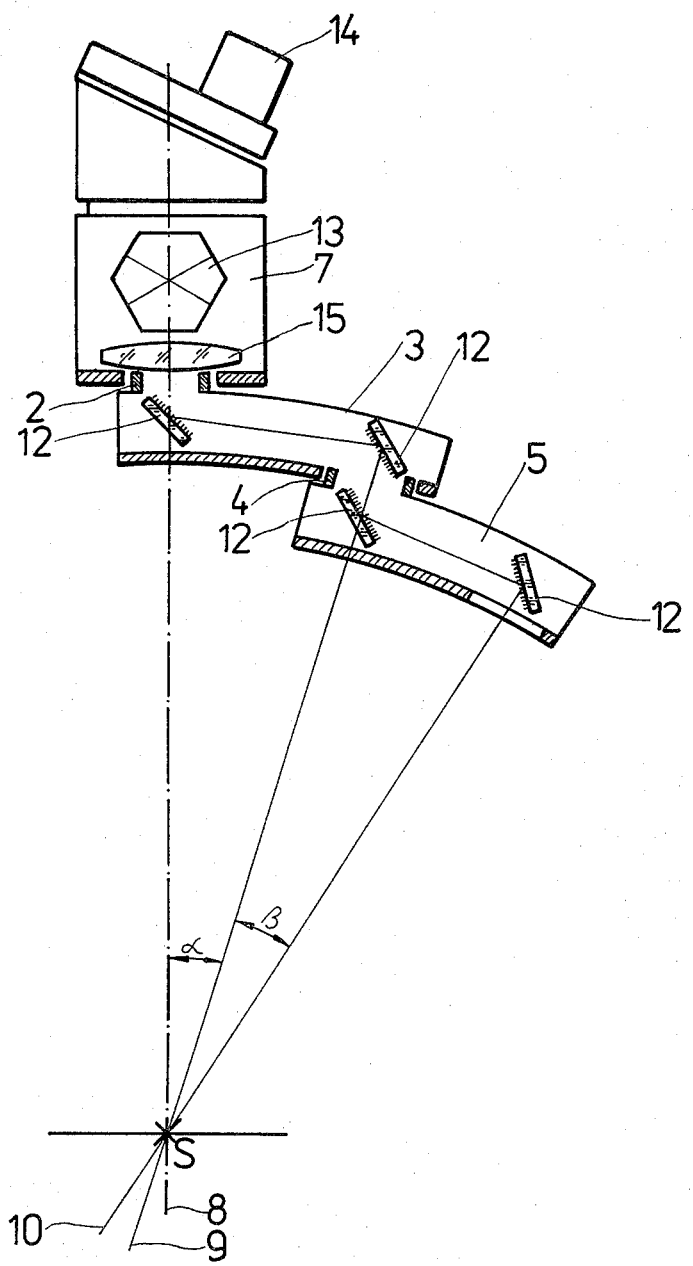

In order that the invention may be more readily understood reference is made to the accompanying drawings which illustrate diagrammatically and by way of example two embodiments thereof and where FIG. 1 is a schematic view of a joint for an observation device the optical path of beam being omitted, and FIG. 2 a schematic view of a joint including means for directing the optical path of beam.

In FIG. 1 a microscope is partially shown comprising a stage 1 and a joint member 3 the one end portion of which is connected thereto via a pivot bearing 2. The other end portion of said joint member 3 is connected via a pivot bearing 4 to the one end portion of a further joint member 5. The other end portion of the latter supports a microscope 7 via a pivot bearing 6. The axial extension 8 of the pivot of the bearing 2, the axis 9 of the pivot of bearing 4, an axis 10 of the pivot of bearing 10, the latter partially coinciding with the axis of the microscope 7, intersect, in a point of intersection S in an object plane 11, thereby including an angle $\alpha$ and $\beta$, respectively. When the microscope is operative it is feasible to fold the optical axis beam which coincides partially with the axis 10 of the pivot bearing 4 in such a manner that at any desired rotations about the three pivot axes 8, 9, 10, the observation beam is such inclined to the object, for example, to point S, that the object does not migrate out of the field of view and the image of the object is not reversed.

In FIG. 2 a two-arm joint member 3, 5 is seated for rotation in bearings 2, 4 of a stereo-microscope 7, which comprises a means 13 for varying the magnification, a microscope objective 15 and an eyepiece 14. The joint members 3, 5, already described in connection with FIG. 1 are provided with two couples of plane reflectors.

The joint member 3 is attached to the microscope 7 in such a manner that the axis of rotation S coincides with the axis of the microscope 7 objective. The pivot connection between the two joint members 3, 5 permits an intersection of the axes of rotations 9 and 8 in an object point S, thereby including an angle $\alpha$. Four reflectors 12 are arranged relative to the joint members 3, 5 in such a manner that the object side portion of an optical axis 10 is imaged through the joint members 3, 5 to the axis 9 to intersect at S including an angle $\beta$.

Thus a continuous inclination adjustment within an angular range of from $\alpha+\beta \ldots \alpha-\beta$ is feasible by swivelling the two joint members 3, 5 about the axes 8 and 9 without the necessity of tilting the eyepiece 14, thus the operator needs not to follow with his head or body the movements of the device as otherwise required.

I claim:

1. A joint for an observation device comprising
a device mount,
at least two joint members,
an observation device,
a first pivot, a second pivot and a third pivot,
  said first pivot having a non-displaceable axis of rotation substantially at right angles relative to the object plane,
  said second pivot having a first displaceable axis of rotation,
  said third pivot having a second displaceable axis of rotation,
  said first pivot seating for rotation one of the two joint members via one end portion of the latter relative to said mount,
  said second pivot seating for rotation via one end portion the other of the two joint members to the other end portion of said one joint member,
  said third pivot seating for rotation said other joint member via the other end portion of the latter to said observation device,
  said non-displaceable axis of rotation,
  said first and second axis of rotation intersecting in a common point of intersection in the observation plane,
  said non-displaceable axis of rotation and said first axis of rotation, and said first axis of rotation and said second axis of rotation, respectively, include a constant angle, and
means for directing an observation beam within the members mentioned hereinbefore.

2. A joint for an observation device comprising
a device mount,
at least two joint members,
an observation device,
a first and a second pivot
  said first pivot having a non-displaceable axis of rotation substantially at right angles relative to the object plane,
  said second pivot having a first displaceable axis of rotation,
  said first pivot seating for rotation one of the two joint members via one end portion of the latter relative to said observation device,
  said second pivot seating for rotation via one end portion the other of the two joint members to the other end portion of said one joint member,
  said non-displaceable axis of rotation and said first axis of rotation intersecting in a common point of intersection in the observation plane,
means for directing an observation beam within the members mentioned hereinbefore,
  said observation beam emitting from out of the observation device partially coinciding with said non-displaceable axis of rotation,
  the portion of said observation beam between the means for directing said observation beam in said first joint member and the respective means in said second joint member coinciding with said first axis of rotation,
  the portion of said observation beam directed by said directing means in said second joint member intersecting in said common point of intersection,
  the latter beam portion and said first displaceable axis of rotation,
  said first displaceable axis of rotation and said non-displaceable axis of the rotation, respectively, include a constant angle.

3. A joint for an observation device as claimed in claim 1 or 2, wherein said means for directing said observation beam are constituted of couples of reflectors inclinedly arranged in each end portion of said first and second joint member.

* * * * *